US00PP31547P3

(12) United States Plant Patent
Hansen

(10) Patent No.: US PP31,547 P3
(45) Date of Patent: Mar. 10, 2020

(54) ***SEDUM* PLANT NAMED 'SUPERSTAR'**

(50) Latin Name: ***Sedum* hybrid**
Varietal Denomination: Superstar

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 114 days.

(21) Appl. No.: 15/932,171

(22) Filed: Feb. 14, 2018

(65) Prior Publication Data

US 2019/0254218 P1 Aug. 15, 2019

(51) Int. Cl.
*A01H 5/02* (2018.01)
*A01H 6/32* (2018.01)

(52) U.S. Cl.
USPC ..... Plt./479
CPC ..... *A01H 6/328* (2018.05)

(58) Field of Classification Search
USPC ..... Plt./479, 373
CPC ... A01H 5/02; A01H 5/00; A01H 5/10; A01H 6/328; A01H 6/749; A01H 5/12; A01H 6/32; A01H 6/00
See application file for complete search history.

(56) References Cited

U.S. PATENT DOCUMENTS

PP22,457 P2 * 1/2012 Hansen ..... A01H 5/02 Plt./479
PP26,591 P2 * 4/2016 Deng ..... A01H 5/12 Plt./373
PP26,595 P2 * 4/2016 Hansen ..... A01H 5/02 Plt./479

OTHER PUBLICATIONS

Germania Seed Company Walters Gardens Bare Root and Plug Perennials 2017, retrieved on Jan. 28, 2019, retrieved from the Internet at https://www.germaniaseed.com/pdf/2018/749_walters.pdf, pp. 1, 19, 22. (Year: 2017).*
Washingon County Cooperative Extension Service 2017 University of Kentucky College of Agriculture Food and Environment, vol. 13, Issue 8/9, 8 pp. (Year: 2017).*

* cited by examiner

*Primary Examiner* — June Hwu

(57) ABSTRACT

The new and distinct cultivar of perennial *Sedum* plant named 'Superstar' is characterized by tight-forming compact clumps with small-sized, greyed-purple glaucous foliage on vertical to slightly arching branching stems flower stems that resist falling over and opening up in the center of the plant throughout the growing season. Numerous stems produce a multitude of flowers beginning light rosy-pink effect darkening with age to reddish purple and completely covering the top and sides of the plant. The new plant is useful for the landscape in containers, as specimen or en masse.

2 Drawing Sheets

Botanical designation: *Sedum* hybrid.
Cultivar denomination: 'Superstar'.

BACKGROUND OF THE INVENTION

The present invention relates to a new and distinct cultivar of *Sedum* plant, botanically known as *Sedum* and hereinafter referred to by the cultivar name 'Superstar'. There are over 300 recognized species of the genus *Sedum*.

The new *Sedum* plant is a selection from a planned breeding program conducted by the inventor, at a wholesale perennial nursery in Zeeland, Mich., USA.

The new *Sedum* plant was selected as a single seedling from an insect pollinated cross in late summer of 2012 between a selection of *Sedum cauticola* (not patented) as the female or pod parent and the proprietary unreleased mutation known as "SRF-SED-282-F 'Sunset Cloud'" (not patented) as the male or pollen parent. *Sedum* 'Superstar' was assigned the breeder code number 12-34-105 to keep it separated from among thousands of other seedlings of this and other crosses when it progressed through the initial trial phase in the fall of 2014. The selected single seedling clone was originally selected for it strong, healthy, upright growth, colorful foliage and flowers.

Asexual reproduction of *Sedum* 'Superstar' by vegetative shoot tip cuttings at a wholesale perennial nursery in Zeeland, Mich., USA since the spring of 2015, has shown that the unique features of this new *Sedum* plant are stable and reproduced true to type in successive generations.

No plants of *Sedum* 'Superstar' have been sold or disclosed by this or any other name, in this country or anywhere in the world, with the exception of that which was either derived directly or indirectly from the inventor and disclosed within one year of the filing of this application.

SUMMARY OF THE INVENTION

Plants of *Sedum* 'Superstar' have not been observed under all possible environmental conditions. The phenotype may vary somewhat with variations in environment such as temperature, available water, fertility and light intensity without, however, any variation in genotype.

The following traits have been repeatedly observed and are determined to comprise the unique characteristics of *Sedum* 'Superstar' and distinguish it as a new and distinct autumn stonecrop plant unique from all other autumn stonecrop plants known to the inventor:

1. Tight-forming compact clumps with vertical to arching stems.
2. Center stems remain erect throughout the growing season produce full habit.
3. Rounded, greyed-green to greyed-purple, glaucous foliage.
4. Numerous, branched, greyed-purple stems produce light rosy-pink flower clusters darkening to reddish-purple and completely covering the top and sides of the plant.

In comparison with the female parent, the new plant has more rounded, fleshy and greyed-purple colored foliage; the inflorescences are more compact with flowers having thinner petals of strong purplish red; and the habit is stiffer and more upright. Compared with the male parent, the new plant has less brownish-red-colored foliage and the flowers are more vibrant reddish purple. The nearest comparison variety known to the inventor is 'Dazzleberry' U.S. Plant Pat. No. 22,457. Compared with 'Dazzleberry', the new plant is slightly taller in flowering size height and has deeper and more vibrant colored flowers. The new plant is more rounded in habit, with more stems and less reddish colored foliage compared with 'Dark Magic' U.S. Plant Pat. No. 27,619. 'Superstar' is has more greyed greenish purple foliage and the flowers are a strong purplish-red compared with 'Firecracker' U.S. Plant Pat. No. 26,595. The foliage of the new plant is more rounded, less dentate distally and more greyed than 'Marina' U.S. Plant Pat. No. 26,191. The copending 'Popstar' has lighter blue-green foliage without the smoky gray overlay, and the flowers are a lighter pink forming dark pink fruit.

BRIEF DESCRIPTION OF THE PHOTOGRAPHS

The photograph of the new plant demonstrates the unique traits and the overall appearance of *Sedum* 'Superstar'. The colors are as accurate as reasonably possible with color reproductions of this type. Variations in ambient light spectrum, source and direction may cause the appearance of minor variation in color. The plants used in the photograph were one and three-year-old plants grown in an open, full-sun trial garden at a wholesale perennial nursery in Zeeland, Mich. with supplemental water and fertilizer when needed. No plant growth regulators or pinching have been used.

DETAILED BOTANICAL DESCRIPTION

Figure 1:
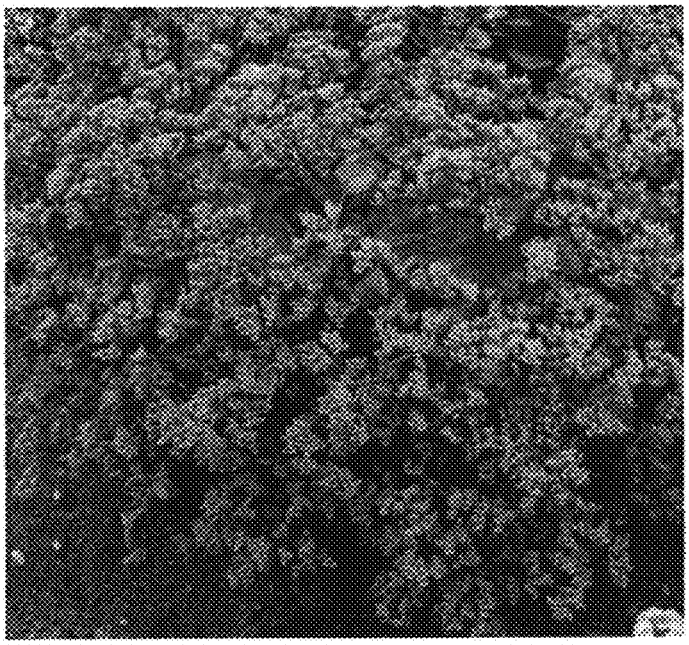
FIG. 1 shows the plant in early stages of flowering with foliage.
Figure 2:
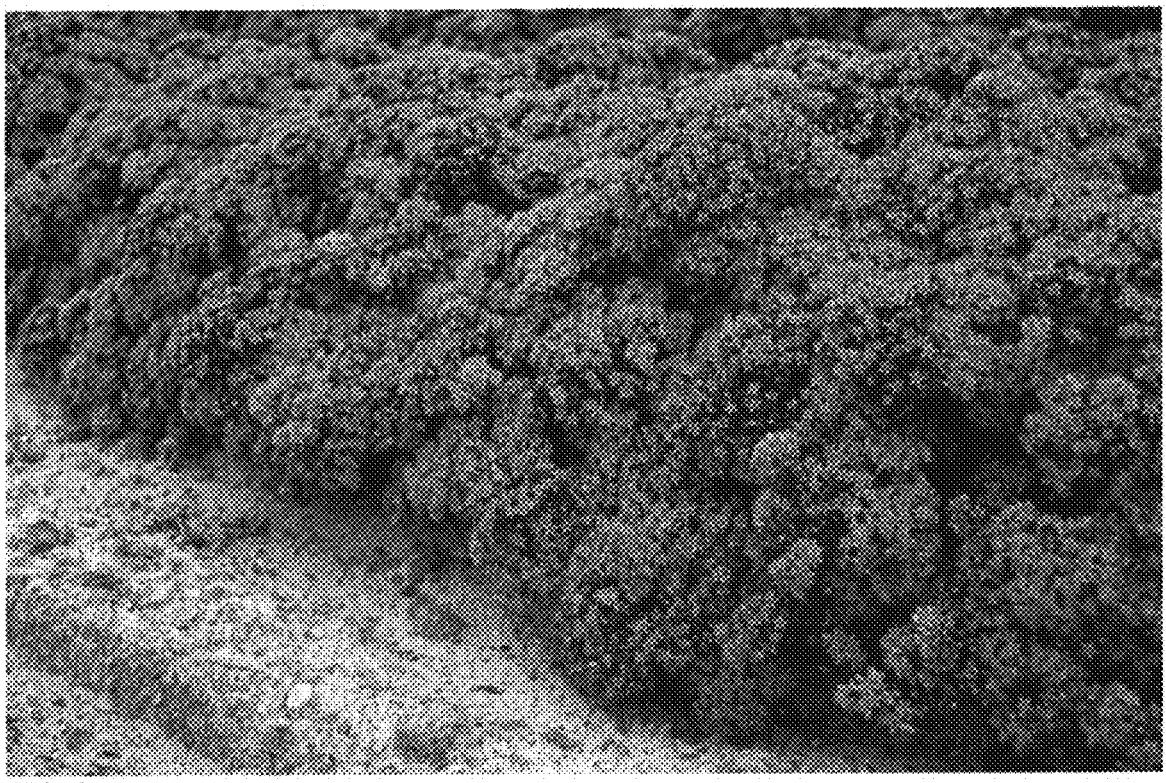
FIG. 2 shows the plant in full flower.
Figure 3:
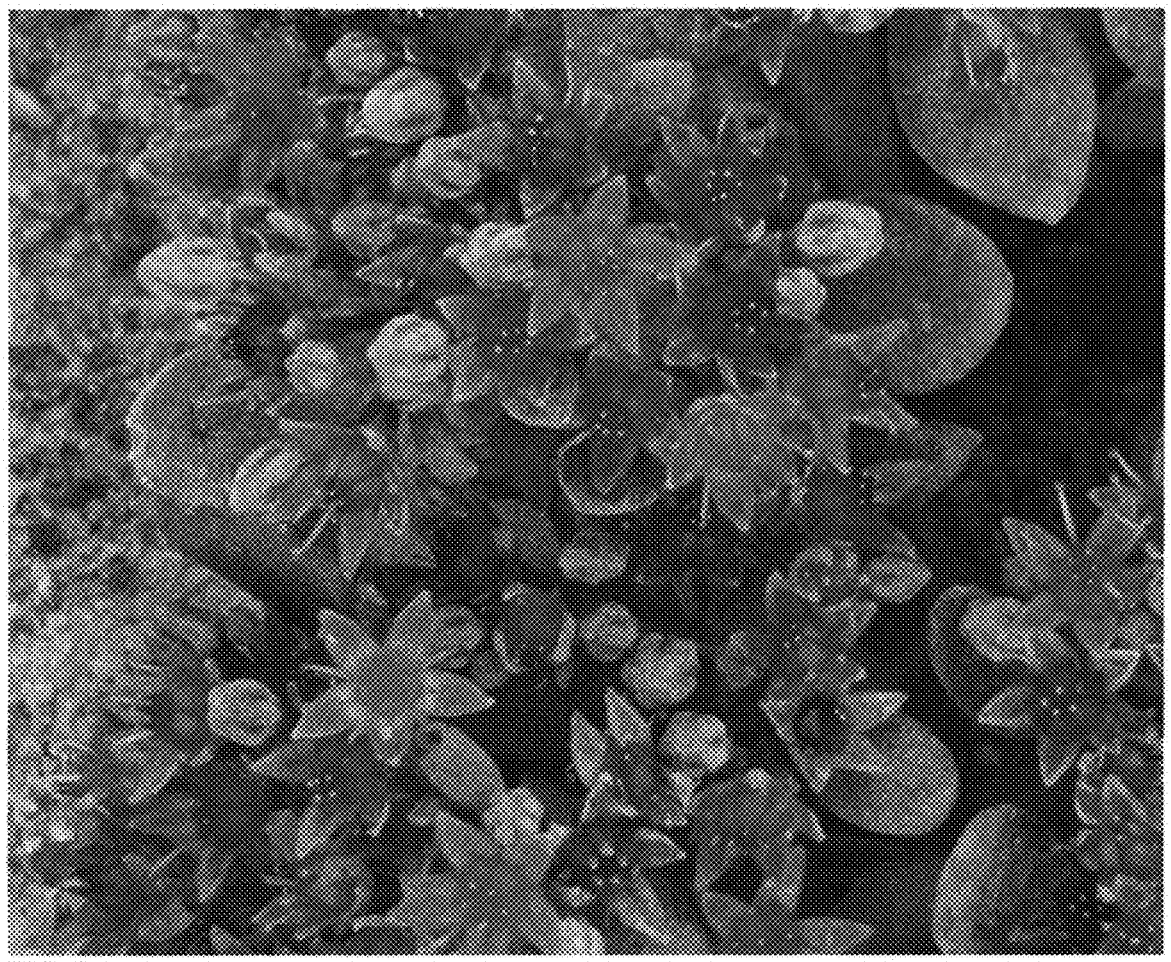
FIG. 3 shows a close-up of the flower and buds.

The following is a detailed description of three-year-old plants of the new cultivar as grown outdoors in a full sun trial plot at a wholesale nursery in Zeeland, Mich. No plant growth regulators or pinching have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Botanical designation: *Sedum* hybrid;

Cultivar denomination: 'Superstar';

Parentage: *Sedum cauticola* as the female or seed parent; "SRF-SED-282-F 'Sunset Cloud'" as the male or pollen parent;

Asexual propagation: Stem tip cuttings and division;

Time to initiate roots: About two weeks;

Time to finish a 3.8 liter flowering container: About three months in the summer from a rooted 2.5 cm plug;

Root description: Thick, fleshy; freely branching; creamy white to light tan in color.

Plant habit: Winter-hardy herbaceous perennial; clumping mound; stems stiff and upright to arching arising from a dense crown; dense and full, not opening in center later in the season; flower heads freely branching;

Growth rate: Moderately vigorous;

Plant size: About 28.5 cm tall and 75.0 cm wide in full flower;

Stems: Terete, glaucous, glabrous; diameter at base average about 3.5 mm and about 21.0 cm long from base to initial branches; internodes average about 8.0 mm; about 80 stems per plant;

Stem color: Nearest a blend between RHS 184D and RHS N187B;

Lateral branches: Glaucous; primary branches about 3.0 mm diameter and about 7.5 cm long;

Lateral branch color: Nearest blend between RHS 186C and RHS N187C;

Foliage: Ovate-orbicular; alternate to sub-opposite; simple; smooth, glabrous, glaucous on both surfaces; distally sessile; thick, fleshy and succulent; apex bluntly acute to rounded; base rounded; margin irregularly and shallowly dentate, primarily in distal one half of leaf, about 3.0 mm to 6.0 mm apart; decreasing in size distally; attitude outward;

Foliage size: To about 4.0 cm long, 3.5 cm across and 2.2 mm thick; average about 3.6 cm long, 3.1 cm across and 2.0 mm thick;

Foliage color: Young adaxial blend between RHS 122B and RHS 189B with blush toward margins of nearest RHS N186B, young abaxial between RHS 122B and RHS 189B with blush toward margins of nearest RHS N186B; mature adaxial nearest RHS 146C with blush of nearest RHS N186C, mature abaxial nearest RHS 146C;

Petiole: Sessile;

Venation: Palmate, barely distinguishable; slightly raised abaxial;

Vein color: Abaxial and adaxial veins same as surrounding leaf tissue;

Flower: Stellate, actinomophic; pentamerous; persistent; attitude upright to outwardly in terminal compound cymes; about 7.0 mm across and 4.0 mm deep;

Flower number: About 2,000 to 4,000 flowers per plant;

Fragrance: None detected;

Flowering season: Beginning mid-August to mid-September in Zeeland, Mich.; able to be forced to flower in greenhouse out of season with about 2 months of growth following 9 weeks of vernalization;

Longevity: Flower cymes remain effective for about three weeks on the plant and one week as cut flowers; individual flowers persistent and effective for about two weeks;

Flower buds about one day prior to opening: Broadly ellipsoidal with five angular sides, semi-carinate; apex broadly acute; base rounded; about 3.7 mm diameter and about 4.5 mm long; shallowly longitudinally sulcate;

Flower bud color: Longitudinally striped alternately with between RHS 75D and RHS 75C and between RHS 71D and RHS 71C; color of buds about ten days prior to opening blend between RHS N187C and RHS 188C with stripes nearest RHS 71A exposed between sepals;

Inflorescence: About 6.5 cm tall from first branch and about 8.5 cm across; up to about 100 flowers per inflorescence;

Petals: Typically five, broadly-lanceolate; acute apex, base fused, margin entire; glabrous and lustrous abaxial and adaxial; average about 4.5 mm long and about 2.2 mm across at fusion;

Petal color: Adaxial nearest a blend between RHS N57C and RHS 61C at anthesis darkening to nearest RHS 60A in maturity; abaxial along longitudinal margins lighter than RHS 63D with midrib between RHS 64B and RHS 64C;

Calyx: With five sepals, fused at base; adpressed to petals, about 2.7 mm long and about 12.0 mm diameter;

Sepals: Campanulate; lanceolate; acute apex; fused base; margin entire; glabrous and glaucous both abaxial and adaxial; about 2.7 mm long and about 2.5 mm wide at fused base;

Sepal color: Abaxial and adaxial nearest a blend between RHS N187C and RHS N77D;

Peduncles: Terete; slightly glaucous, glabrous; stiff and flexible; freely branching; upright to slightly outwardly; with branches to about 70 degrees from perpendicular; about 8.0 cm long and 3.0 mm diameter;

Peduncle color: Proximal portions nearest RHS 187C and distal portions nearest RHS 186C;

Pedicels: Terete; glabrous, slightly glaucous; strong and stiff, yet flexible; about 4.5 mm long and 0.7 mm diameter;

Pedicel color: Blend between RHS N187C and RHS 186C;

Androecium: Typically ten stamens;

*Filaments.*—Outwardly; about 4.0 mm long and about 0.2 mm diameter; color initially nearest RHS 63C and darkening to between RHS 61A and RHS 61B.

*Anthers.*—Basifixed, longitudinal; globose to ellipsoid; about 0.7 mm long and 0.6 mm diameter; color nearest RHS N77D.

*Pollen.*—Moderate in quantity; color nearest RHS 18B.

Gynoecium: Typically five; ellipsoidal proximally and conic in distal one third; about 4.5 mm long and 1.2 mm diameter;

*Style.*—Terete; about 0.7 mm long and 0.5 mm diameter at point of attachment to ovary; glabrous; color at anthesis nearest RHS 61C darkening to nearest RHS 61A on old flowers.

*Stigma.*—Minute, globose; about 0.2 mm diameter and 0.2 mm long; color nearest RHS N155B.

*Ovary.*—Ellipsoidal, nearly terete, acutely tapering at apex to style; base truncate; lustrous; about 3.7 mm long and 1.2 mm diameter; color at anthesis between RHS 61C and RHS 61D and nearest RHS 60A after pollen dehisced.

Fruit: Ventrally dehiscent follicle; about 3.5 mm long and 3.2 mm across; color at maturity nearest RHS 177A;

Seed: Sparse; fine; lanceolate; about 1.0 mm long and less than 0.2 mm across; color between RHS 165A and RHS 165B;

Disease and pest resistance: Plants of the new *Sedum* 'Superstar' is xeromorphic and grow best with good drainage, full sun and moderate to low fertility. 'Superstar' is cold hardy from USDA zones 3 to 9 and has tolerated temperatures of at least 35 degrees C. 'Superstar' tolerates heavy rains and wind and is not prone to develop an open center later in the season as many other *Sedum* cultivars do. Other pest and disease resistance and tolerance outside that normal for *Sedum* is not known.

It is claimed:

1. The new and distinct perennial *Sedum* plant named 'Superstar' as herein described and illustrated.

* * * * *